United States Patent
Wikner

(10) Patent No.: US 7,125,555 B2
(45) Date of Patent: Oct. 24, 2006

(54) ORAL PREPARATION CONTAINING SEAWEED FOR REDUCTION OF PLAQUE AND CALCULUS

(75) Inventor: Sune Wikner, Umeå (SE)

(73) Assignee: SDC SweDenCare AB, Kiruna (SE)

( * ) Notice: Subject to any disclaimer, the term of this patent is extended or adjusted under 35 U.S.C. 154(b) by 0 days.

(21) Appl. No.: 10/399,770

(22) PCT Filed: Sep. 27, 2001

(86) PCT No.: PCT/SE01/02083

§ 371 (c)(1),
(2), (4) Date: Apr. 24, 2003

(87) PCT Pub. No.: WO02/34279

PCT Pub. Date: May 2, 2002

(65) Prior Publication Data

US 2004/0022806 A1    Feb. 5, 2004

(30) Foreign Application Priority Data

Oct. 27, 2000  (SE) .................................... 0003907

(51) Int. Cl.
*A61K 36/00* (2006.01)
(52) U.S. Cl. ................................. 424/195.17
(58) Field of Classification Search ............ 424/195.17
See application file for complete search history.

(56) References Cited

U.S. PATENT DOCUMENTS

| | | | | |
|---|---|---|---|---|
| 4,581,233 A | * | 4/1986 | Herve et al. | 424/195.17 |
| 4,775,525 A | * | 10/1988 | Pera | 424/58 |
| 4,857,331 A | * | 8/1989 | Shaw et al. | 424/440 |
| 5,539,133 A | * | 7/1996 | Kohn et al. | 554/20 |
| 5,650,412 A | * | 7/1997 | Kim et al. | 514/252.13 |
| 6,013,632 A | * | 1/2000 | Jones et al. | 514/17 |
| 6,224,871 B1 | * | 5/2001 | Hastings et al. | 424/195.17 |
| 6,338,856 B1 | * | 1/2002 | Allen et al. | 424/442 |
| 6,495,530 B1 | * | 12/2002 | Daniels | 514/56 |

FOREIGN PATENT DOCUMENTS

| | | | |
|---|---|---|---|
| JP | 56113269 A | * | 9/1981 |
| JP | 56117777 A | * | 9/1981 |
| WO | 8907437 A1 | | 8/1989 |
| WO | 0013531 A2 | | 3/2000 |

OTHER PUBLICATIONS

Vacca et al. ("The Antibacterial Activity of an Extract Obtained from *Ascophyllum nodosum,*" Journal of the American Pharmaceutical Association (1912-1977) (1954), 43, 24-6).*
Patent Abstracts of Japan, abstract of JP 5-139979 A, (Lotte Co Ltd), Jun. 8, 1993.
Patent Abstracts of Japan, abstract of JP 1-186813 A, (Nippon Flour Mills Co Ltd), Jul. 26, 1989.

* cited by examiner

*Primary Examiner*—Christopher Tate
*Assistant Examiner*—S. B. McCormick-Ewoldt
(74) *Attorney, Agent, or Firm*—Bacon & Thomas, PLLC

(57) ABSTRACT

An oral preparation for reduction of mammalian, e.g. human, cat or dog, plaque and/or calculus, such as bacterial plaque, arteriosclerotic plaque, atherosclerotic plaque, pleural plaque, dental calculus, renal calculus, biliary calculus, and prostatic calculus, contains a *Ascophyllum sp.*, especially *A. nodosum*, seaweed or an extract thereof. The oral preperation is suitable for use in prophylactic and/or therapeutic method of treating plaque and/or calculus in a mammalian individual.

18 Claims, 3 Drawing Sheets

ORAL PREPARATION CONTAINING SEAWEED FOR REDUCTION OF PLAQUE AND CALCULUS

The present invention relates to an oral preparation for reduction of mammalian plaque and/or calculus. More precisely, the invention relates to the use of an *Ascophyllum sp.* seaweed or an extract thereof for the manufacture of an oral preparation for reduction of mammalian plaque and/or calculus, to a unite dose of an oral preparation comprising as an active ingredient a an *Ascophyllum sp.* seaweed or an extract thereof, and to a prophylactic and/or therapeutic method of treating plaque and/or calculus in a mammalian individual.

BACKGROUND

Dental calculus is an inconvenience that affects mammals, such as humans, cats and dogs. Dental calculus is considered by professionals to be calcified bacterial deposits. It is considered to appear where removal of the deposits has failed. It is very strongly attached to the dental surface and it is impossible for an ordinary person to remove it by himself. The only method hitherto know for removing dental calculus is that the dentist or the dental hygienist mechanically brakes it loose with an instrument or vibrates it loose with a supersonic apparatus. Dental calculus gives no pain but the removal thereof often does. It makes oral hygiene more difficult and should be removed.

Plaque is a necessity for formation of dental calculus and for development of caries. However, all plaques do not develop calculus, probably due to some protective mechanism in saliva and/or the periodontal exudate. There is not sufficient knowledge of the character of such a protective mechanism. The composition of the diet may be of importance.

Everyone does not get dental calculus. Despite a miserable oral hygiene some persons may live their whole life without getting any. The reason for this is unknown but it can be assumed that the chemical composition of the saliva plays an important role. Therefore, it should be possible to combat the formation of dental calculus with chemical means. Many attempts have been made to administer chemical preparations that were expected to locally influence the process. Hitherto none has been successful.

DESCRIPTION OF THE INVENTION

The present invention provides a means to reduce, or even eliminate, not only bacterial plaque and dental caries but also arteriosclerotic plaque, atherosclerotic plaque, pleural plaque, renal calculus, biliary calculus, and prostatic calculus.

The invention is based on empirical studies on dog and human which have established that dental calculus is released after a few weeks consumption of coated tablets containing meal of seaweed. They were swallowed without letting them first exert any local effect in the mouth. Therefore it can be concluded that the effect on the dental calculus depends on influence mediated by the blood, saliva and/or the fluid coming from gum pockets. Evidently chemical components from the tablet, via some of the fluids, broke the chemical bonds that keep the dental calculus attached to the dental surface. However, the mechanism of action is not known.

Both in the initial empirical studies and in the experiments below the seaweed used is an *Ascophyllum sp.* namely *A. nodosum*. The analyzed composition of *Ascophyllum nodosum* is given in Table 1. This seaweed has been commercially available all over Europe for more than 30 years. It contains a large number of nutrients and may be regarded as a dietary supplement.

Thus, one aspect of the invention is directed to the use of an *Ascophyllum sp.* seaweed or an extract thereof for the manufacture of an oral preparation for reduction of mammalian plaque and/or calculus.

In this specification and claims, it is intended that the extract of *Ascophyllum sp.* seaweed should be interpreted as any synthetic or isolated part of the seaweed that is capable of reducing mammalian plaque and/or calculus.

In a preferred embodiment of the invention the mammal is selected from a human, a cat and a dog.

In another embodiment the oral preparation is selected from a powder, suspension, tablet, coated tablet and capsule. Since the taste of the seaweed is not considered to be attractive, the taste is preferably masked by providing the seaweed in a coated tablet or capsule, or by adding a spice or aroma to the powder, suspension or uncoated tablet. Commonly used additives required to form the respective oral preparations should be used.

In a preferred embodiment of the invention, the plaque is selected from bacterial plaque, arteriosclerotic plaque, atherosclerotic plaque, and pleural plaque, and the calculus is selected from dental calculus, renal calculus, biliary calculus, and prostatic calculus.

In a presently most preferred embodiment the seaweed is *Ascophyllum nodosum*.

For example, the *Ascophyllum nodosum* seaweed may have an analyzed chemical composition of:

20–26% of sulphated uronic acids in esterified form, 5–8% of Mannitol, 2–5% of Laminaran, 5–15% of Fucoidin, 2.5–3.5% of S, 2–3% of K, 3–4% of Cl, 3–4% of Na, 0.5–1% of Mg, 1–3% of Ca, 0.1–0.15% of P, and 40–100 mg/kg of Br, 1–10 mg of Co, 1–10 mg Cu, 150–1000 mg of Fe, 10–50 mg of Mn, 700–1200 mg of I, 20–200 mg of Zn, 0.3–1 mg of Mo, 2–5mg of Ni, 15–50 mg of Ba, 1.5–3 mg of V and 500–2000 mg/kg of Ascorbic acid, 150–300 mg/kg of Tocopherols, 30–60 mg/kg of Carotenes, 10–30 mg/kg of Niacin, 0.1–0.4 mg/kg of Biotin, 0.2–1 mg/kg of Folic acid, 5–10 mg/kg of Riboflavine, 1–5 mg/kg of Thiamine, 0.004 mg/kg of Vitamin B12, and 10 mg/kg of Vitamin K.

Another aspect of the invention is directed to a unit dose of an oral preparation comprising as an active ingredient a mammalian plaque and/or calculus reducing amount of an *Ascophyllum sp.* seaweed or an extract thereof In a preferred embodiment the mammalian plaque and/or calculus reducing amount of an *Ascophyllum sp.* seaweed is 250 mg-1 g of seaweed per unit dose. The *Ascophyllum sp.* seaweed is preferably *Ascophyllum nodosum*.

Still another aspect of the invention is directed to a prophylactic and/or therapeutic method of treating plaque and/or calculus in a mammalian individual in need thereof, comprising administration of a unite dose of an oral preparation according to the invention to said individual.

The invention will now be further illustrated with reference to the description of drawings and experiments, but the scope of protection is not intended to be limited to the disclosed embodiments of the invention.

DESCRIPTION OF THE DRAWINGS

In FIGS. 1 and 2, the OHI-s is an oral hygiene index that describes the extension of plaque or calculus on a tooth surface. It is subdivided into four classes: 0 indicating no plaque, 1 indicating plaque on <⅓ of the surface, 2 indicating plaque on <⅔ and 3 indicating plaque on >⅔ of the tooth surface.

Experiments

In addition to the described initial empirical studies a number of experiments were conducted as will be disclosed in the following.

The oral preparation used in the experiments is a unite dose in the form of a coated tablet, called CalcOFF, and it consists of

| | |
|---|---|
| Dry powder of *Ascophyllum nodosum* | 250 mg |
| Dicalcium phosphate | 130 mg |
| Microcrystalline cellulose | 116.8 mg |
| Magnesium stearate | 3.2 mg |

The experiments were conducted with 30 adult patients who used to be calculus formers and who had oral calculus present at baseline. They got free samples of the CalcOFF and agreed to consume two tablets a day for two months.

One dentist recorded the extension of supragingival calculus and plaque on teeth 26, 31 and 11 (Greene and Wermillion index, i.e. oral hygiene index=OHI-s) at baseline and after two months. The ORI-s results were recorded as plaque index (PLA) and calculus index (CAI), respectively.

Statistical method: The differences between values recorded at baseline and two months later were statistically evaluated by Analysis of variance.

Figure 1:
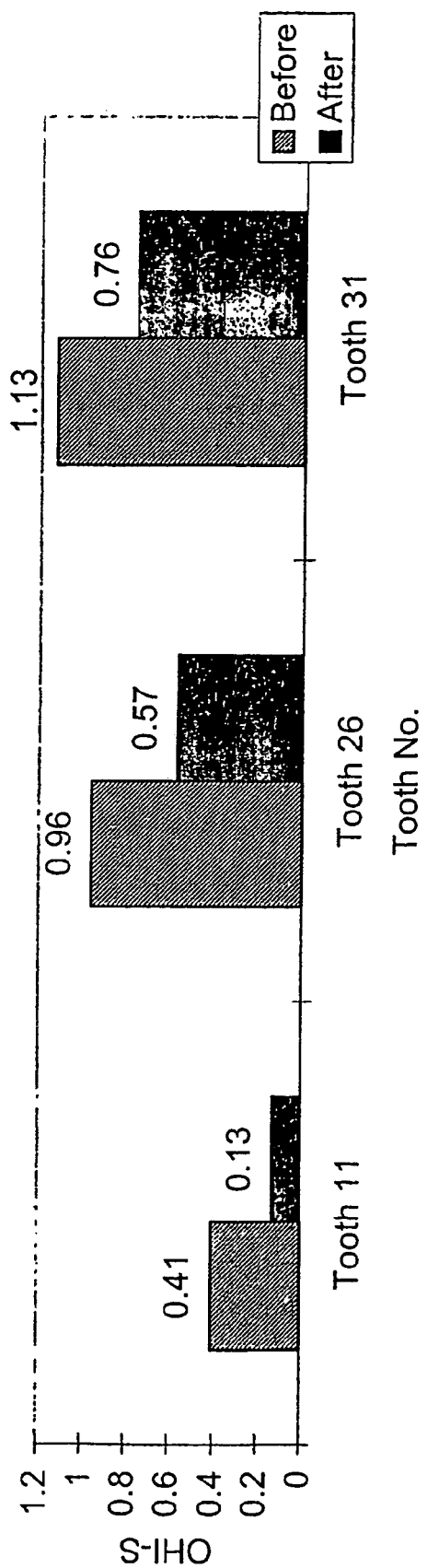
FIG. 1 is a diagram that shows the extension of calculus on 3 teeth in 30 persons after 2 months consumption of CalcOFF, a tablet according to the invention.

Results: The Tables 2 and 3, and the FIGS. 1 and 2, demonstrate that the extension of both plaque and calculus was strongly and significantly reduced on all examined teeth. It is emphasized that the data accounted for in Table 3 to some extent are based on the dentists subjective judgement.

Figure 3:
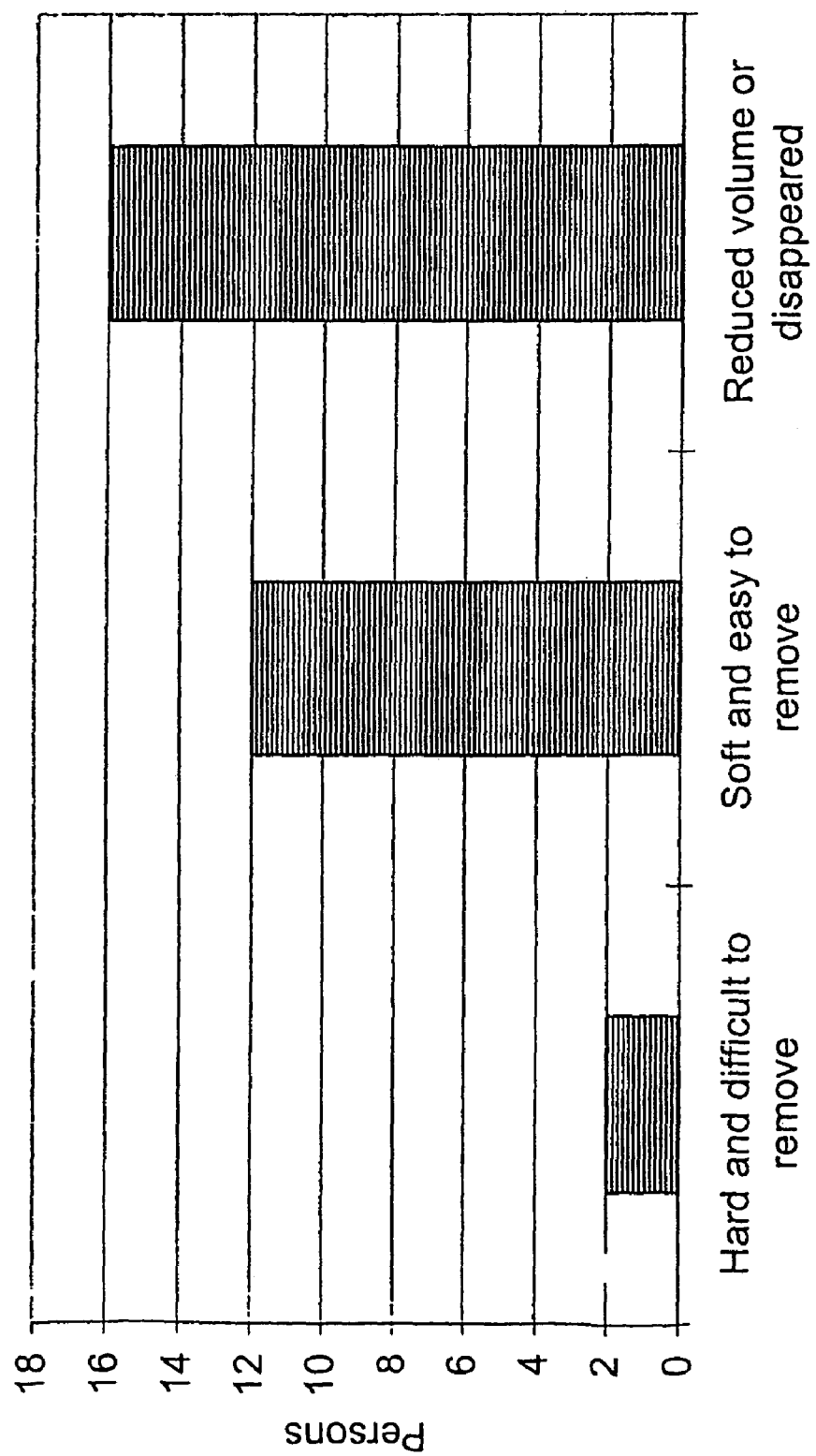
FIG. 3 is a diagram that shows the quality of dental calculus in 30 persons after 2 months consumption of CalcOFF.

As shown in FIG. 3 the effect of the CalcOFF tablet on calculus differed between individuals. In 16 persons the calculus disappeared or the extension of it was reduced. In 12 persons, only little reduction was recorded but the calculus was extremely soft and easy to remove, even by the patient. No effect was recorded in two cases. The differing effect is most likely due to different levels of mineralization.

At the two month examination some of the patients who still had calculus accepted to increase from two to four CalcOFF tablets a day for another eight weeks. This experiment is still running but it is evident that they are loosing calculus more rapidly now. Thus it seems that the effect is dose dependent.

In other cases the calculus was removed by the dentist two months after baseline and the patients continued to eat the CalcOFF tablet. Formation of new calculus was either nil or considerably slower compared to previous years.

Figure 2:
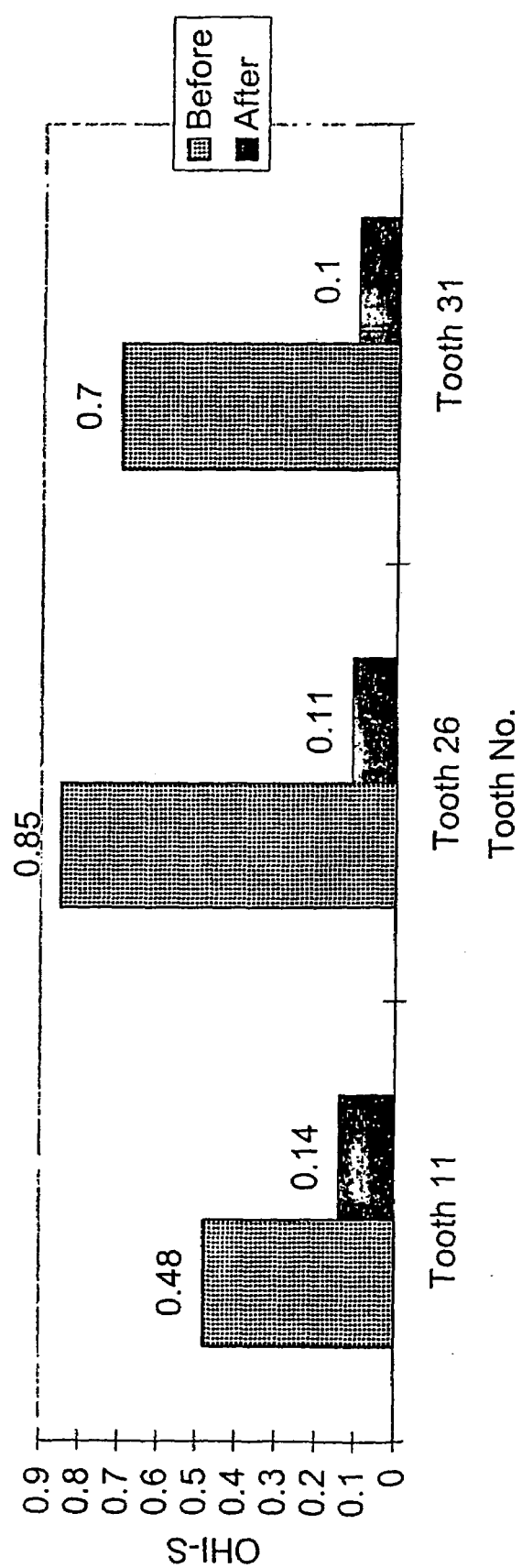
FIG. 2 is a diagram that shows the extension of plaque on 3 teeth in 30 persons after 2 months consumption of CalcOFF.

The CalcOFF tablet had a pronounced effect on plaque formation (FIG. 2). Consumption during two months reduced plaque by 71–87 percent. According to Table 2 the difference before and after consumption was highly significant on all three examined teeth. Most likely that effect can be achieved already after a few days consumption of the CalcOFF tablet.

Two of the patients suffered from renal calculus as well. Surprisingly they noticed that they got a precipitation in their urine, indicating degradation of their renal calculus.

These findings indicate that CalcOFF is efficient against other calculus formations in addition to dental calculus and likely efficient against other plaque formations in addition to dental plaque.

The recorded reduction of existing calculus is consistent with the observed plaque reduction and the observation that new calculus formation was unusual during the consumption period.

Daily consumption of this seaweed may reduce the extension of plaque and of calculus in adults having calculus, but also prevent formation of new plaque and calculus.

TABLE 1

The analyzed composition of *Ascophyllum nodosum*

| | |
|---|---|
| Water | 12–15 % |
| Ash | 17–20 % |
| Alginic acid | 20–26 % |
| Mannitol | 5–8 % |
| Laminaran | 2–5 % |
| Fibres | <8 % |
| Protein | 5–10 % |
| Ether extract | 2–4 % |
| Fucoidin | 10 % |
| S | 2.5–3.5 % |
| K | 2–3 % |
| Cl | 3.1–4.4 % |
| Na | 3–4 % |
| Mg | 0.5–0.9 % |
| Ca | 1–3 % |
| P | 0.1–0.15 % |
| Br | 40–100 mg/kg |
| Co | 1–10 mg/kg |
| Cu | 1–10 mg/kg |
| Fe | 150–1000 mg/kg |
| Mn | 10–50 mg/kg |
| I | 700–1200 mg/kg |
| Zn | 20–200 mg/kg |
| Mo | 0.3–1 mg/kg |
| Ni | 2–5 mg/kg |
| Ba | 15–50 mg/kg |
| V | 1.5–3 mg/kg |
| Ascorbic acid | 500–2000 mg/kg |
| Tocopheroles | 150–300 mg/kg |
| Carotene | 30–60 mg/kg |
| Niacin | 10–30 mg/kg |
| Biotin | 0.1–0.4 mg/kg |
| Folic acid | 0.2–1 mg/kg |
| Riboflavine | 5–10 mg/kg |
| Thiamine | 1–5 mg/kg |
| Vit. B12 | 0.004 mg/kg |
| Vit. K | 10 mg/kg |

TABLE 2

Extension of dental calculus on teeth No. 26, 31 and 11 in 30 persons before and after two months consumption of CalcOFF.

| | CAI | SD | | |
|---|---|---|---|---|
| Tooth No. 26 | | | | |
| At baseline | 0.96 | 0.527 | | |
| After two months | 0.57 | 0.503 | Diff 41% | P < 0.0021 |
| Tooth No. 31 | | | | |
| At baseline | 1.13 | 0.571 | | |
| After two months | 0.76 | 0.504 | Diff 30% | P < 0.011 |

TABLE 2-continued

Extension of dental calculus on teeth No. 26, 31 and 11 in 30 persons before and after two months consumption of CalcOFF.

|  | CAI | SD |  |  |
|---|---|---|---|---|
| Tooth No. 11 |  |  |  |  |
| At baseline | 0.41 | 0.568 |  |  |
| After two months | 0.14 | 0.350 | Diff 68% | P < 0.009 |

TABLE 3

Extension of plaque on teeth No. 26, 31 and 11 in 30 persons before and after two months consumption of CalcOFF.

|  | PLI | SD |  |  |
|---|---|---|---|---|
| Tooth No. 26 |  |  |  |  |
| At baseline | 0.85 | 0.456 |  |  |
| After two months | 0.11 | 0.362 | Diff 87% | P < 0.0001 |
| Tooth No. 31 |  |  |  |  |
| At baseline | 0.70 | 0.535 |  |  |
| After two months | 0.10 | 0.305 | Diff 86% | P < 0.0001 |
| Tooth No 11 |  |  |  |  |
| At baseline | 0.48 | 0.580 |  |  |
| After two months | 0.15 | 0.362 | Diff 71% | P < 0.001 |

The invention claimed is:

1. A therapeutic method of treating bacterial plaque and/or dental calculus in a mammalian individual in need thereof, comprising administering to said mammalian individual an oral preparation for consumption containing a bacterial plaque and/or dental calculus reducing amount of *Ascophyllum nodosum* seaweed as the active ingredient.

2. A method according to claim 1, wherein the mammal is selected from the group consisting of a human, a cat and a dog.

3. A method according to claim 1, wherein the oral preparation is selected from the group consisting of a powder, suspension, tablet, coated tablet and capsule.

4. A method according to claim 1, wherein the *Ascophyllum nodosum* seaweed has an analyzed chemical composition of:
20–26% of sulphate uronic acids in esterified form, 5–8% of Mannitol, 2–5% of Laminaran, 5–15% of fucoidin, 2.5–3.5% of S, 2–3% of K, 3–4% of Cl, 3–4% of Na, 0.5–1% of Mg, 1–3% of Ca, 0.1–0.15% of P, and 40–100 mg/kg of Br, 1–10mg of Co. 1–10mg Cu, 150–1000mg of Fe, 10–50mg of Mn, 700–1200mg of I, 20–200mg of Zn, 0.3–1 mg of Mo, 2–5mg of Ni, 15–50mg of Ba, 1.5–3mg of V and 500–2000 mg/kg of Ascorbic acid, 150–300 mg/kg of Tocopherols, 30–60 mg/kg of Carotenes, 10–30 mg/kg of Niacin, 0.1–0.4 mg/kg of Biotin, 0.2–1 mg/kg of Folic acid, 5–10 mg/kg of Riboflavine, 1–5 mg/kg of Thiamine, 0.004 mg/kg of Vitamin B12, and 10mg/kg of Vitamin K.

5. A method according to claim 1, wherein the bacterial plaque and/or dental calculus reducing amount of the *Ascophyllum nodosum* seaweed is 250 mg-1 g per unit dose of the oral preparation.

6. A method according to claim 5 for treating dental calculus.

7. A method according to claim 5 for treating bacterial plaque.

8. A method according to claim 1 wherein the active ingredient consists essentially of the *Ascophyllum nodosum* seaweed.

9. A method according to claim 1 wherein the active ingredient consists of the *Ascophyllum nodosum* seaweed.

10. A method according to claim 6 for eliminating existing calculus wherein the oral preparation is a coated tablet.

11. A method accordingly to claim 10 wherein the coated tablet comprises the active ingredient, dicalcium phosphate, microcrystalline cellulose and magnesium stearate.

12. A method according to claim 11 wherein the active ingredient is *Ascophyllum nodosum* seaweed which has an analyzed chemical composition of:
20–26% of sulphate uronic acids in esterified form, 5–8% of Mannitol, 2–5% of Laminaran, 5–15% of fucoidin, 2.5–3.5% of S, 2–3% of K, 3–4% of Cl, 3–4% of Na, 0.51% of Mg, 1–3% of Ca, 0.1–0.15% of P, and 40–100 mg/kg of Br, 1–10mg of Co. 1–10mg Cu, 150–1000mg of Fe, 10–50mg of Mn, 700–1200mg of I, 20–200mg of Zn, 0.3–1 mg of Mo, 2–5mg of Ni, 15–50mg of Ba, 1.5–3mg of V and 500–2000 mg/kg of Ascorbic acid, 150–300 mg/kg of Tocopherols, 30–60 mg/kg of Carotenes, 10–30 mg/kg of Niacin, 0.1–0.4 mg/kg of Biotin, 0.2–1 mg/kg of Folic acid, 5–10 mg/kg of Riboflavine, 1–5 mg/kg of Thiamine, 0.004 mg/kg of Vitamin B12, and 10mg/kg of Vitamin K.

13. A method according to claim 11 wherein the tablet is administered twice a day by swallowing the coated tablet.

14. A method according to claim 12 wherein the tablet is administered twice a day by swallowing the coated tablet.

15. A method according to claim 14, wherein the mammalian individual is a human.

16. A method according to claim 1 for eliminating existing calculus.

17. A method according to claim 2 wherein the animal is a dog or a cat and wherein the oral preparation is administered as a powder.

18. A method according to claim 3 wherein the oral preparation is a capsule.

* * * * *